United States Patent
Kerimo et al.

(10) Patent No.: US 11,079,325 B2
(45) Date of Patent: Aug. 3, 2021

(54) METHODS AND SYSTEMS FOR POINT-OF-CARE COAGULATION ASSAYS BY OPTICAL DETECTION

(71) Applicant: Instrumentation Laboratory Company, Bedford, MA (US)

(72) Inventors: Josef Kerimo, Concord, MA (US); Hansong Zeng, Acton, MA (US); Ron Scharlack, Brookline, MA (US); Gert Blankenstein, Cambridge, MA (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 0 days.

(21) Appl. No.: 14/696,756

(22) Filed: Apr. 27, 2015

(65) Prior Publication Data
US 2015/0316533 A1 Nov. 5, 2015

Related U.S. Application Data

(60) Provisional application No. 61/986,475, filed on Apr. 30, 2014.

(51) Int. Cl.
*G01N 21/53* (2006.01)
*G01N 21/64* (2006.01)
(Continued)

(52) U.S. Cl.
CPC .......... *G01N 21/534* (2013.01); *G01N 21/59* (2013.01); *G01N 21/6408* (2013.01);
(Continued)

(58) Field of Classification Search
CPC .. G01N 21/534; G01N 21/59; G01N 21/6486; G01N 21/7743; G01N 2201/0636; G01N 33/4905; G01N 33/54373
(Continued)

(56) References Cited

U.S. PATENT DOCUMENTS

| 4,964,728 A | 10/1990 | Kloth et al. |
| 5,114,860 A * | 5/1992 | Hayashi ............ G01N 33/4905 356/338 |

(Continued)

FOREIGN PATENT DOCUMENTS

| CN | 101194309 | 6/2008 |
| CN | 101677766 | 3/2010 |

(Continued)

OTHER PUBLICATIONS

Hemker et al., "Calibrated automated thrombin generation measurement in clotting plasma", Pathophysiology of Haemostasis and Thrombosis, 33, Apr. 15, 2003.

(Continued)

*Primary Examiner* — Lyle Alexander
*Assistant Examiner* — Bryan Kilpatrick
(74) *Attorney, Agent, or Firm* — Burns & Levinson LLP

(57) ABSTRACT

This invention relates to an optical system and method for performing turbidity assay, e.g. coagulation of blood or plasma, comprising a standard optical reference, a sample handling structure, a light source and an optical detection unit. The standard optical reference, such as a fluorophore-doped glass, provides constant optical signal under controlled optical conditions. The sample handling structure, such as a microfluidic system with reaction chamber, can be placed beneath or above the standard optical reference. During operation, the coagulating plasma/blood changes its optical absorbance and reflection properties, which results in changes in optical signal that reaches the optical reading unit. The variation of the optical signal, such as fluorescence signal indicates the kinetics of the turbidity varying process, such as plasma/blood coagulation process. This invention is used for performing turbidity assay with optical system, (Continued)

including photometry system, fluorescence system, Raman Spectroscopy system and so on.

21 Claims, 13 Drawing Sheets

(51) Int. Cl.
    *G01N 21/65* (2006.01)
    *G01N 33/49* (2006.01)
    *G01N 21/59* (2006.01)

(52) U.S. Cl.
    CPC ......... *G01N 21/6486* (2013.01); *G01N 21/65* (2013.01); *G01N 33/4905* (2013.01); *G01N 2201/062* (2013.01); *G01N 2201/0636* (2013.01)

(58) Field of Classification Search
    USPC .............................................. 422/73; 436/69
    See application file for complete search history.

(56) References Cited

U.S. PATENT DOCUMENTS

| | | | |
|---|---|---|---|
| 5,525,466 A * | 6/1996 | Slovacek | G01N 21/648 356/243.1 |
| 6,252,664 B1 * | 6/2001 | Barbera-Guillem | G01N 21/59 250/461.1 |
| 6,352,630 B1 | 3/2002 | Frenkel et al. | |
| 8,558,205 B2 | 10/2013 | Ikari et al. | |
| 9,500,589 B2 | 11/2016 | Nakatani et al. | |
| 2002/0064800 A1 | 5/2002 | Sando et al. | |
| 2003/0180191 A1 | 9/2003 | Suzuki et al. | |
| 2005/0101025 A1 * | 5/2005 | Ho | B01L 3/0275 436/86 |
| 2006/0178570 A1 | 8/2006 | Robinson et al. | |
| 2008/0096285 A1 * | 4/2008 | Koyata | G01N 21/59 436/164 |
| 2013/0301051 A1 | 11/2013 | Pogosyan et al. | |
| 2014/0004527 A1 | 1/2014 | Oka et al. | |

FOREIGN PATENT DOCUMENTS

| | | |
|---|---|---|
| CN | 101821610 | 9/2010 |
| CN | 104897599 | 9/2015 |
| EP | 1 496 351 A2 | 1/2005 |
| JP | 2002345787 A | 12/2002 |
| JP | 2011048677 A | 3/2011 |
| WO | 2012096566 | 7/2012 |
| WO | 2012/137506 A1 | 10/2012 |
| WO | 2011/001681 | 12/2012 |
| WO | 2013/161543 A1 | 10/2013 |
| WO | 2015-118843 A1 | 8/2015 |

OTHER PUBLICATIONS

International Preliminary Report on Patentability for International Application No. PCT/US2015/027715, dated Nov. 10, 2016 (10 pages).
Examination report No. 1, Australian Patent Application No. 2015253478, dated Nov. 16, 2017, 3 pages.
Canadian Intellectual Property Office, Office Action, Canadian Application No. 2,946,877, 7 pages.
First Office Action from related Chinese Application No. 201580034415.3, dated Jul. 31, 2018, includes English translation.
Examination Report from related Australian Application No. 2015253478, dated Jul. 27, 2018.
Japanese Office Action, Japanese Patent Application No. 2016-564011, dated Nov. 28, 2018, 3 pages (translations included, 4 pages).
Canadian Office Action, Canadian Patent Application No. 2,946,877, dated Apr. 10, 2019, 5 pages.
Office Action dated Oct. 28, 2020 issued in corresponding Japanese application No. 2019-140602, 3 pages and English translation thereof, 4 pages.
International Search Report and Written Opinion for International Application No. PCT/US2015/027715, dated Jul. 22, 2015, 14 pages.
Final Notice of Reasons for Rejection for Japanese patent application No. 2019-140602, dated May 31, 2021, with English translation (7 pages).

* cited by examiner

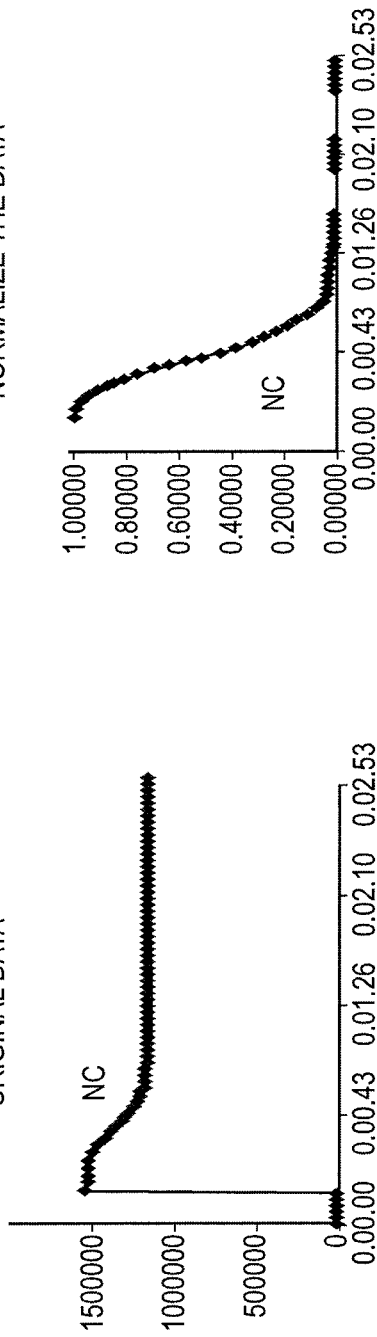
FIG. 13A
FIG. 13B
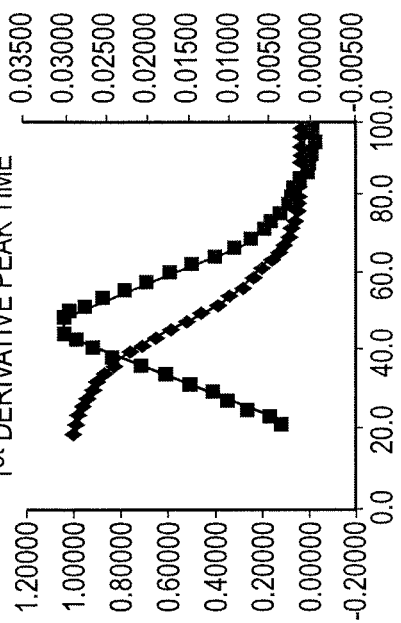
FIG. 13D
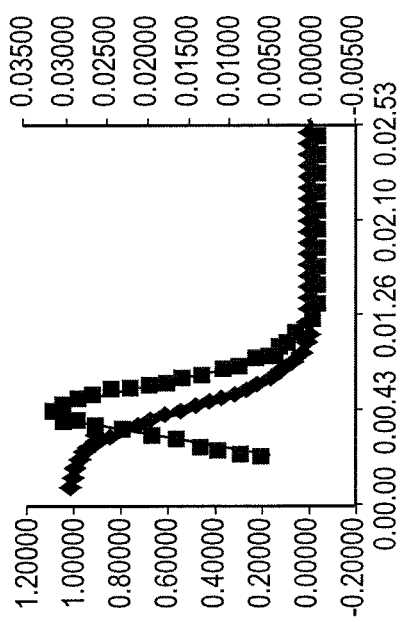
FIG. 13C

ME THODS AND SYSTEMS FOR
POINT-OF-CARE COAGULATION ASSAYS
BY OPTICAL DETECTION

CROSS-REFERENCES TO RELATED APPLICATION

This application claims priority to and benefit of U.S. Provisional Application No. 61/986,475 filed Apr. 30, 2014, the entire contents of which are incorporated by reference herein for all purposes.

FIELD OF THE INVENTION

This invention relates to an optical system and method for detecting coagulation of plasma or blood comprising a standard optical reference, a sample handling structure, a light source and an optical detection unit.

BACKGROUND

Coagulation assays are important tools to monitor a patient's risk of bleeding or thrombosis, both of which could lead to fatal consequences if intervention does not occur promptly and appropriately. This is especially critical in emergency and operation rooms, as a patient's hemostasis health status needs to be understood before proper hemotherapy is administered. Among all the coagulation assays, prothrombin time (PT) and activated partial thromboplastin time (APTT) assays are currently the most popular coagulation tests used in clinics and hospitals.

Instruments performing PT and APTT assays usually contain blood sample preparation mechanisms such as coagulation reagents and optical spectroscopy measurement units. Despite the advantages such as high throughput and good accuracy, these assays have some disadvantages that prevent its application for point-of-care tests. First, (1) due to the complex sample preparation and measurement process, the sampling-to-result time ranges from days to weeks. Such a slow turnaround time cannot meet the near real-time requirement in emergency rooms or other near-patient use. Secondly, (2) a large volume of blood, i.e., more than a milliliter of blood is required with these instruments for proper sample handling and accurate measurement.

Fluorescence-based technologies with state-of-the-art microfluidic sample preparation, such as lab-on-a-chip immunoassay, were developed to solve the above shortfalls. A popular method in the recognized art is to use thrombin or plasmin (both factors are generated during coagulation reaction pathways) specific substrates containing immunoreactive fragments. Upon exposure to thrombin or plasmin, the substrates are cleaved and the immunoreactive fragments are released from the substrate, which generates a fluorescence signal as an indicator of the kinetics of coagulation process. These technologies suffer from poor reliability due to the low efficiency of the chemical reaction and the stability of the immunoreactive fragments. Additionally, the requirement by the industry for quality control in chemical production, instrument manufacturing, and final usage increases the cost of these prior art coagulation assays.

The invention disclosed herein was developed to successfully solve the problems identified in prior art coagulation assays of slow turn-around-time, large sample size requirement, excessive production costs, lack of reagent stability, and inability of prior art coagulation assays to meet the near real-time requirement in emergency rooms or other near-patient use for immediate coagulation assay results.

SUMMARY OF THE INVENTION

The fluorescence based and other coagulation assays according to the invention described below can be used widely in various clinical situations. Centralized large instruments or point-of-care instruments can be developed around these methods to achieve high throughput coagulation assays. Various assays specific to certain factors involved in the coagulation cascade, for example, can be realized with this technology.

More importantly, compact point-of-care devices according to the invention described herein can be developed for emergency room, surgical suites, intensive care units or a physician's office. The rapid response and small sample size requirement of the disclosed invention allow the technology to be used for continuous monitoring of coagulation kinetics, e.g., when hemotherapy is required. In the meantime, the invention can be used with existing immunoassay systems and/or microfluidic systems that are currently used for the diagnosis of heart diseases and cancers of patients, without the need for extensive new instrument development.

In one aspect, the invention is directed to an assay system comprising a reaction chamber for holding a sample, an excitation light source, an optical reference for providing an optical signal, and an optical receiver. The optical reference is positioned to absorb the excitation light and generates the optical signal to the optical receiver.

The reaction chamber according to the invention is positioned to inhibit or enhance the signal generated from the optical reference and detected by the optical receiver. In one embodiment, the reaction chamber holds a sample in the absence of a colorimetric reagent.

The excitation light source provides a specific wavelength ranging, fix example but not limited to, from 20 nm to 5000 nm, 50 nm to 2000 nm, or 100 nm to 1000 nm.

The optical reference according to the assay system is selected from the group consisting of, for example, fluorescence doped glass, stained glass, dyed glass, and materials showing Raman effect. The reaction chamber comprises a lumen, a planar first wall, and a planar second wall. In one embodiment of the reaction chamber, the planar second wall is opposite and parallel to the planar first wall.

In one embodiment of the invention, the planar first wall and the planar second wall are each optically transparent to light in the wavelength range of, for example, about 20 nm to about 5000 nm, or alternatively, in the wavelength range of about 20 nm to about 2000 nm.

In various embodiments of the invention, the reaction chamber is positioned between the optical reference and the optical receiver and excitation light source, or the optical reference is positioned between the reaction chamber and the optical receiver and excitation light source, alternatively the optical reference is positioned between the excitation light source and the reaction chamber, and the reaction chamber is positioned between the optical reference and the optical receiver.

The assay system further comprises an optical receiver that includes a light detector for detecting emission light emitted from the light source or the optical reference, or for detecting reflected or secondary light. In one embodiment, the optical receiver module and light source module are integrated.

In one embodiment, each of the first and second planar walls of the reaction chamber comprise a luminal surface and the first planar luminal surface is coated with one or more reactants. The reaction chamber may further comprise a sample inlet port and a reaction fluid outlet port. The first inlet port may feature a v-shape.

In another aspect, the invention is directed to a method for detecting coagulation. In one embodiment of this aspect of the invention, the method requires:
(i) providing a system comprising an optical reference consisting of a device for generating a calibrated optical signal;
(ii) providing a reaction chamber comprising a chamber for holding a fluid, the chamber comprising a planar first wall and a planar second wall that is opposite and parallel to the planar first wall, and a lumen for holding a fluid, the first and second planar walls of the reaction chamber comprising a luminal surface and the first planar luminal surface is coated with one or more reactants, and an inlet, for example, a V-shaped inlet for introducing a body fluid sample into the reaction chamber;
(iii) transmitting excitation light from a light source through the fluid in the reaction chamber to an optical reference;
(iv) measuring emission light from the optical reference transmitted through the fluid in the reaction chamber to an optical detector;
(v) comparing the measured emission light to a predetermined standard for determining coagulation time in the system.

In another embodiment, the method requires
(i) providing a system comprising an optical reference consisting of a device for generating a calibrated optical signal;
(ii) providing a reaction chamber comprising a chamber for holding a fluid, the chamber comprising a planar first wall and a planar second wall that is opposite and parallel to the planar first wall, and a lumen for holding a fluid, the first and second planar walls of the reaction chamber comprising as luminal surface and the first planar luminal surface is coated with one or more reactants, and an inlet, for example, a V-shaped inlet for introducing a body fluid sample into the reaction chamber;
(iii) transmitting excitation light from a light source through the optical reference to the fluid in the reaction chamber;
(iv) measuring reflected emission light from the optical reference transmitted to an optical detector; and
(v) comparing the measured emission light to a predetermined standard for determining coagulation time in the system.

In yet another embodiment, the method requires
(i) providing a system comprising an optical reference consisting of a device for generating a calibrated optical signal;
(ii) providing a reaction chamber comprising a chamber for holding a fluid, the chamber comprising a planar first wall and a planar second wall that is opposite and parallel to the planar first wall, and a lumen for holding a fluid, the first and second planar walls of the reaction chamber comprising a luminal surface and the first planar luminal surface is coated with one or more reactants, and an inlet, for example, a V-shaped inlet introducing a body fluid sample into the reaction chamber;
(iii) transmitting excitation light from a light source through the optical reference;
(iv) the optical reference generates a secondary light which passes through the reaction chamber;
(v) measuring the secondary light by the optical detector; and
(vi) comparing the measured secondary light to a predetermined standard for determining coagulation time in the system.

The foregoing and other objects, features, and advantages of the invention will become apparent from the following, more particular description of the preferred embodiments of the invention.

BRIEF DESCRIPTION OF THE DRAWINGS

The invention is described with particularity in the appended claims. The further advantages of the invention described herein may be better understood by referring to the following description taken in conjunction with the accompanying drawings.

FIG. 13A-D shows an exemplary mathematical method to process the optical data to obtain quantitative coagulation time.

DESCRIPTION

Figure 1:
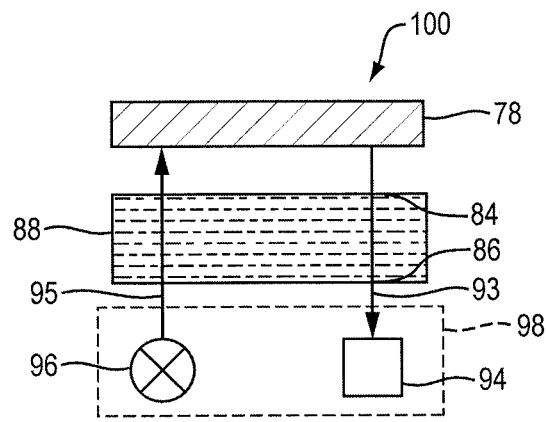
FIG. 1 illustrates a double absorbance optical configuration for the coagulation system to absorb both excitation light from a light source and returning light from optical reference during coagulation of a plasma or blood sample according to one embodiment of the invention.

In one aspect, the invention relates to a system for detecting coagulation of a patient plasma or blood sample in a reaction chamber, for example, a chamber of a microfluidic device. The system includes an optical reference part, such as but not limited to a standard fluorescence element, such as but not limited to a fluorophore-doped glass, a polymer film or sheet containing intrinsic fluorescence that is used to generate a fluorescence reference signal. The positioning of the fluorescence element and the coagulating blood/plasma sample is configured to vary the light energy that reaches and/or leaves the optical reference. With such configuration, the system according to the invention de-couples the fluorescence signal from chemical reactions. The variation of the fluorescence signal indicates the kinetics of the plasma/blood sample coagulation process.

The coagulation detection system according to the invention is used for performing coagulation assays, for example, with fluorescence detection. As a point-of-care (POC) coagulation immunoassay system, the sample preparation can be implemented in a microfluidic cartridge, allowing small sample volume, i.e., less than a milliliter, preferably less than 100 microliters, and low manufacturing cost. The invention can be used for types of wet chemical assays where a change in adsorption, turbidity during the assay is used for detection and quantification of an analyte in a sample. Typical wet chemical assays are immunochemical, enzymatic, clotting assays, affinity based, and nucleic acid based assays. Different optical detection methods may be used in various embodiments such as but not limited to turbidity, absorption, reflectance, fluorescence intensity, time resolved fluorescence, NIR and others. Compared to traditional coagulation assay tools such as optical spectroscopy or lab-on-a-chip assay systems, the coagulation system according to the invention has at a minimum the following advantages:

(1) the enhanced portability of the system and fast turn-around time allowing point-of-care applications;

(2) the system's handling of a sample requires only a small amount, i.e. less than a milliliter of patient blood or plasma, preferably below 100 microliters;

(3) no indicators like those typically required in state-of-the-art fluorescence assays such as fluorophore reagents or colorimetric reagents need to be added into the assay. This simplifies the assay protocol by reducing the assay handling steps which would otherwise require immunoreactive reagents, intra-assay chemicals, and chemical reactions. The fluorescence signal generated according to the invention is only a function of the coagulation reaction and requires no fluorophores added into the sample, resulting in lower cost and lower background interference;

(4) the decoupling of fluorescence signal and chemical reaction, together with using a standard fluorescence element, allows easy and reliable quality control;

(5) the system according to the invention described herein can be realized in any fluorescence system, various liquid handling systems including microfluidics, robotic, and manual liquid transportation systems allowing rapid and cost-effective adoption and integration with other biomarker detection systems, such as, but not limited to solid phase immunoassays for the quantification of other analytes in blood such as cardiac markers like troponin I or markers providing additional information to clotting parameters such as D-Dimer. D-dimer tests are ordered, along with other laboratory tests and imaging scans, to help rule out the presence of a thrombus;

(6) the cost of the cartridge which includes the various embodiments of the optical system according to the invention is sufficiently low to be disposable which reduces the risk of cross-contamination. The cartridge can be manufactured preferably in polymers such as polystyrene or cycloolefines, by manufacturing methods, preferably injection molding or hot embossing;

(7) different wavelengths may be used for the light source and signal detection thereby reducing background interference. The light source may be selected from but is not limited to the group consisting of a laser, a mercury arc lamp, and an LED. Wavelengths range from, for example, about 20 nM to about 5000 nM, about 50 nM to about 2000 nM, about 100 nm to about 1000 nM.

Optical Configuration

Figure 2:
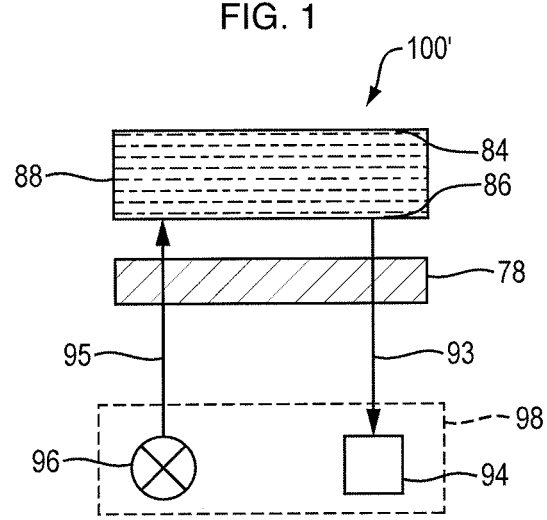
FIG. 2 illustrates a reflection optical configuration for the coagulation system to entrap excitation light at the interface between sample and optical reference to enhance optical signal generated in the optical reference during coagulation of a plasma or blood sample according to another embodiment of the invention.
Figure 3:
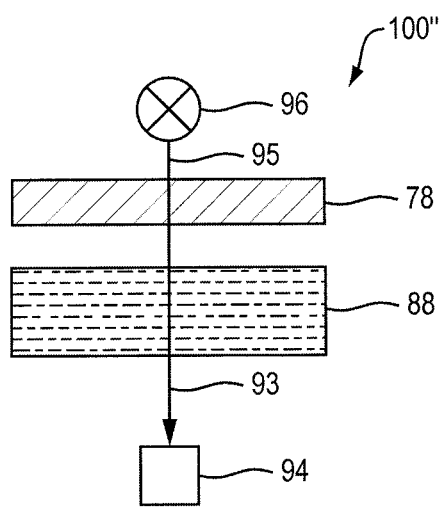
FIG. 3 illustrates a transmission configuration for the coagulation system to absorb the light emitted from the optical reference excited by the light source during coagulation of a plasma or blood sample according to another embodiment of the invention.

Various optical configurations, with different arrangements of optical reference and sample reaction chamber, are disclosed for various turbidity assays, e.g. blood coagulation assays. The schematics of each configuration according to embodiments of the invention are illustrated in FIGS. 1, 2 and 3, and the operation principles are described below.

1. Double Absorbance Optical Configuration

As shown in FIG. 1, according to one embodiment of the invention, a double absorbance optical configuration system 100 has a fluorescence module 98, a reaction chamber 88, and a fluorescence reference 78. In one embodiment, a fluorescence module 98 integrates both light source 96 and fluorescence detection unit 94, for example, but not limited to a detection system to measure time resolved fluorescence (TRF) using an LED (360 nm), for example, for excitation and a photodetector, such as a photo diode or a multi pixel photon counter (MPPC, to quantify the fluorescence emission.

With continued reference to FIG. 1, according to one embodiment of the invention, the double absorbance optical configuration system 100 has a light source 96, an optical detection unit 94, an optical reference 78 and a reaction chamber 88. During operation, the light 95 from the light source 96 and the returning light 93 from the optical reference 78 both transmit through the sample in the reaction chamber 88 and is absorbed due to turbidity change of the sample, plasma or blood, for example. The source or excitation light 95 and returning or emission light 93 can have same or different wavelengths. The optical reference 78 can be realized with various optical technologies, such as but not limited to generic photometry, fluorescence, Raman spectroscopy time-resolved fluorescence, and surface enhanced Raman spectroscopy. In one embodiment, a fluorescence-based method is used for blood coagulation time measurement with light source being LED, optical reference being a fluorescence glass, returning light being emission from the fluorescence element, the sample being plasma, and the optical detection unit being a fluorescence detector. In this embodiment, when the plasma coagulates in the reaction chamber, the fluorescence signal read at the optical detection unit is reduced due to increased optical absorbance by the coagulated plasma.

With continued reference to FIG. 1, the reaction Chamber 88 encloses a plasma or blood sample and reagent(s) for a particular target coagulation assay. The reaction chamber 88 comprises a first wall 86 and a second wall 84 that is opposite to the first wall and is positioned between the optical reference 78 and the light source 96 and detector 94. The first wall 86 is optically transparent to a light of specified wavelength and is closer to the fluorescence module 98 than the second wall 84. The second wall 84 is optically transparent to the light with specified wavelengths and is positioned opposite and parallel to the first wall 86 and closer to the fluorescence reference 78 than the first wall 86. A reagent added to the plasma or blood sample in the reaction chamber 88 enables the coagulation reaction in the reaction chamber 88.

The optical reference 78 is, for example, but not limited to, a fluorescence-doped glass, or fluorophores immobilized on the surface of the second, opposite wall 84 of the reaction chamber 88. In the double absorbance optical configuration embodiment, the fluorescence reference 78 is positioned on the side of the reaction chamber 88 that is opposite to the fluorescence module 98 as illustrated in FIG. 1. The purpose of the optical reference 78 is to provide a calibrated optical signal at a specific wavelength.

During operation, once the plasma or blood sample coagulation process starts, more and more fibrin is formed thereby increase the turbidity of the plasma or blood sample in the reaction chamber 88. As a result, the transmission of the excitation light 95 through the sample is reduced and the excitation of fluorescence molecules on the optical reference 78 is inhibited. In addition, the reduced emission light 93 from the optical reference 78 is absorbed further when it passes through the sample in the reaction chamber 88 to the fluorescence module 98 where it is detected and measured by the fluorescence detector 94. The combined effect of the two absorbance processes, i.e., the first absorbance as the excitation light 95 passes through the reaction chamber 88 to the fluorescence reference 78, and the second absorbance as the emission light 93 passes from the optical reference 78 through the reaction chamber 88, is expected to produce a signal change detected by the optical detector 94. The signal change indicates the coagulation process of the sample in the reaction chamber 88. As a result, a decrease of the fluorescence signal detected by the optical detector 94 in this double absorbance optical configuration indicates that the coagulation process has begun. The relative change of the signal with time gives information about the coagulation process (kinetics, slope). For the proper calculation of the different coagulation parameters such as PT, APTT, the maximum and minimum signal is determined.

2. Reflection Optical Signal

FIG. 2 illustrates a reflection optical configuration of the turbidity system 100' according to another embodiment of the invention in which the fluorescence reference 78 is positioned between the reaction chamber 88 and the fluorescence module 98.

With continued reference to FIG. 2, the reflection optical configuration system 100', like the double absorbance optical configuration system 100' described above, comprises a fluorescence module 98, a reaction chamber 88, and a fluorescence reference 78. In one embodiment of the reflection optical configuration, the fluorescence module 98 integrates both light source 96 and fluorescence detection unit 94, for example, but not limited to a fluorescence reader from Horiba Instruments Inc. (Kyoto, Japan) that has an LED (360 nm) light source and a MPPC (a multi pixel photon counter) detector.

The reaction chamber 88 encloses a plasma or blood sample, and reagent(s) for a specified target coagulation assay and typically has a plurality of planar walls, at least two of which are parallel and opposite. The optical reference 78 is positioned between the reaction chamber 88 and the excitation light source 96, and optical receiver 94. For example, the reaction chamber 88 comprises a first wall 86 and a second wall 84 opposite to the first wall 86. In a preferred embodiment the first wall 86 and the second wall 84 are parallel to one another. Alternatively the first wall and the second wall may be placed at an angle to one another, for example, at a 45° angle. In the reflection optical configuration, the first wall 86 is optically transparent to a light of specified wavelength and is positioned closer to the fluorescence reference 78 than the second wall 84. The second wall 84 is positioned opposite and parallel to the first wall 86 and farther away from the fluorescence reference 78 than the first wall 86. The second wall 84 may or may not be optically transparent. A reagent added to the plasma or blood sample in the reaction chamber 88 enables the coagulation reaction in the reaction chamber 88.

The optical reference 78 is, for example, but not limited to, a fluorescence-doped glass, or fluorophores immobilized on the surface of the first wall 86 of the reaction chamber 88. In this embodiment, the fluorescence reference 78 is positioned between the reaction chamber 88 and the fluorescence module 98 as illustrated in FIG. 2. The purpose of the fluorescence reference 78 is to provide a calibrated fluorescence signal.

During operation, once the plasma or blood sample coagulation process starts, more and more fibrin is formed thereby increase the turbidity of the plasma or blood sample in the reaction chamber 88.

As illustrated in FIG. 2, in the reflection optical configuration, the excitation light 95 first reaches the optical reference 78 and then transmits through the sample in the reaction chamber 88. In other words, one portion of the excitation light 95 excites fluorescence of the optical reference 78 before transmission through the reaction chamber 88, while the remaining portion of the excitation light 95 transmits through the sample in the reaction chamber 88. As coagulation of the plasma or blood sample in the reaction chamber 88 initiates and propagates, and the quantity of fibrin increases in the sample, the energy distribution of the two light portions, i.e., transmitted and reflected light, is varied due to the change of the sample's transmission property. Namely, the transmission of the excitation light 95 is inhibited, and more light is trapped at the interface of the fluorescence reference 78 and the first wall 86 of the reaction chamber 88 to excite more fluorophores. As a result, an increase of the fluorescence signal detected by the optical detector 94 in this configuration indicates that the coagulation process has begun. The clotting time can be determined by, for example, the slope of the clotting curve which is calculated by the first derivative of the clotting curve (maximum value of the first derivative is giving the start time for coagulation) as shown in FIG. 12. Maximum (start of the reaction, time point zero) and minimal signal (coagulation completed) are needed to determine the clotting time.

3. Transmission Optical Configuration

FIG. 3 illustrates yet another optical configuration of the system 100". The optical reference 78 is arranged between the light source 96 and sample reaction chamber 88, and the reaction chamber 88 is placed between optical reference 78 and optical detection unit 94. During operation, the optical reference 78 is excited by the source light 96 and emits a secondary light 93, such as fluorescence signal. The secondary light 93 passes through the reaction chamber 88 and is absorbed due to turbidity change of the sample. The optical detector 94 reads the signal of the secondary light 93 from the optical reference 78. The quantitative value of the signal represents the kinetics of the coagulation reaction.

Figure 4:
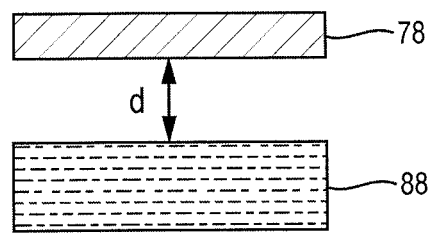
FIG. 4 illustrates that the distance between optical reference and sample fluid (d) can vary from 0 to a large value, typically 0 to 200 mm with all the configurations described with respect to FIGS. 1, 2 and 3.
Figure 5A:
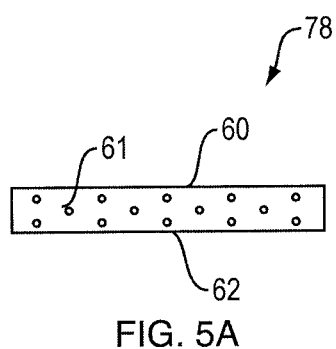
FIGS. 5A-E illustrate a method to make the optical reference with various compositions, including (A) dope optical agents, such as but not limited to fluorescence molecules, particle, dyes, inside a substrate material such as, but not limited to plastics, glass, and silicon; (B) chemically assemble a layer of optical agents on the first surface of the substrate; (C) chemically assemble a layer of optical agents on the opposite surface of the substrate; (D) coating a layer of optical agents on the first surface of a substrate by either physical or chemical method; (E) coating a layer of optical agents on the opposite surface of the substrate by either physical or chemical method.
Figure 5B:
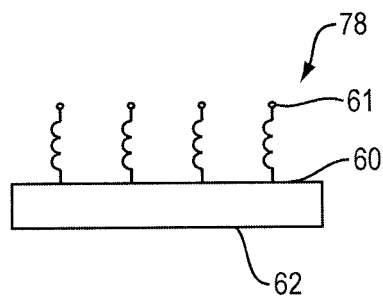
Figure 5C:
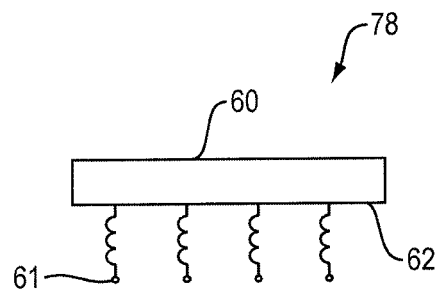
Figure 5D:
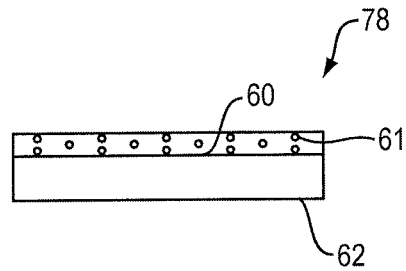
Figure 5E:
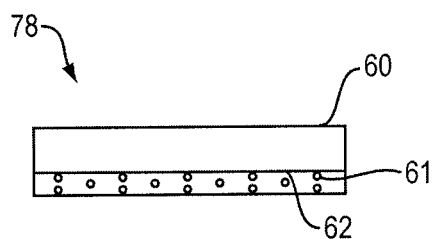

FIG. 4 illustrates that the distance (d) between the optical reference 78 and the sample in the lumen 83 of the reaction chamber 88 can vary from about 0 to about 200 mm with each configuration described above with respect to FIGS. 1, 2 and 3.

FIG. 5 illustrates exemplary configurations of the optical reference 78. Using optical reference with fluorescence properties as a non-limiting example, the optical agents 61 can be made by embedding fluorescence molecules, particles or other carriers into a plastic, glass or silicon material substrate 78 (FIG. 5A). Alternatively, the optical fluorescence agents can be chemically or physically coated on the surface of the substrate, either on the top 60 or bottom 62 surface, i.e., first surface 60 or second surface 62 opposite the first surface, or both. For example, as illustrated in FIG. 5(B) a layer of optical agents 61 may be chemically assembled on the first surface 60 of the substrate by physical means or chemical means; in FIG. 5(C) a layer of optical agents 61 may be chemically assembled on the second surface 62 of the substrate by physical or chemical means; in FIG. 5(D), a layer of optical agents 61 may be coated on the first surface 60 of the substrate by chemical or physical means; or, in FIG. 5(e), a layer of optical agents 61 may be coated on the second surface 62 of the substrate by chemical or physical means.

FIG. 6 illustrates various exemplary arrangements of the reaction chamber 88 and the optical reference 78. The optical reference 78 can be an integral part of the reaction chamber 88, for example, by being embedded in the top or bottom part of the enclosed wall 64 of the reaction chamber 88, or, alternatively, the optical reference can be a separate part placed outside above or outside below the reaction chamber 88 to form suitable optical configurations according to the invention. Preferably the long axis of the optical reference 78 is perpendicular to the excitation light. Alternatively the excitation light may be at an angle to the long axis of the optical reference 78.

Figure 6A:
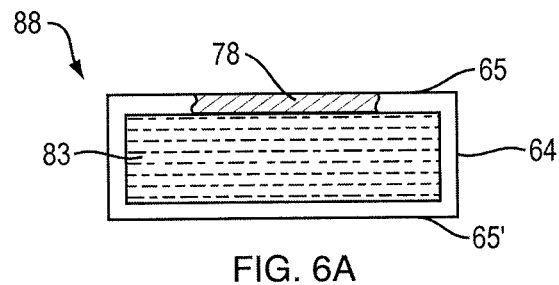
FIGS. 6A-G illustrate exemplary configurations for integrating the optical reference with the reaction chamber of the sample handling device: (A) embedding the optical reference in the first wall of the integral reaction chamber; (B) bonding a flat optical reference to form the first wall of the reaction chamber with the cavity of the reaction chamber in the bottom part; (C) bonding the optical reference to the remaining portions of the reaction chamber illustrated in 6B except the bottom portion; (D) placing the optical reference outside the enclosed reaction chamber as a separate part; (E) embedding the optical reference within the wall opposite to the first wall of the integral reaction chamber; (F) bonding the flat optical reference to form the opposite wall of the reaction chamber with the cavity of the reaction chamber in the remaining portion; (G) bonding the optical reference to the remaining portions of the reaction chamber illustrated in 6F except the first wall.
Figure 6B:
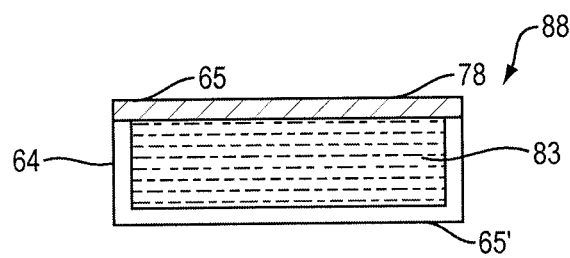

FIG. 6A illustrates an exemplary planar optical reference 78 embedded in the first wall 65 of the enclosing wall 64 of the reaction chamber 88, according to one embodiment. Alternatively, FIG. 6B illustrates a planar optical reference 78 bonded to and forming the first wall 65 of the reaction chamber 88 with the lumen 83 of the reaction chamber 88 on the inside of the first wall 65 of the reaction chamber 88. In a preferred embodiment the long axis of the optical reference 78 is perpendicular to the light source or alternatively at an angle up to about 45°.

Figure 6C:
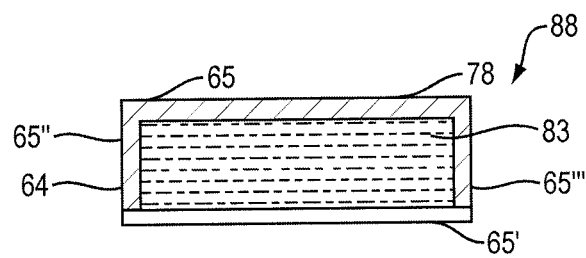

In another embodiment, illustrated in FIG. 6C, the optical reference 78 forms three walls, 65, 65", 65''' of the reaction chamber 88 while only the second wall 65', opposite wall 65, is not a portion of the optical reference 78.

Figure 6D:
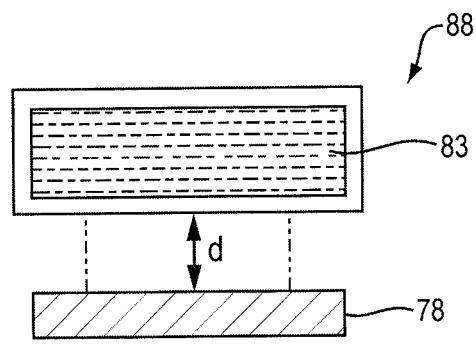
Figure 6E:
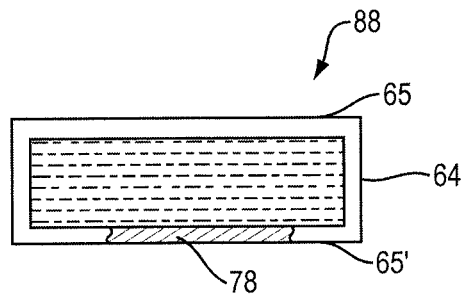
Figure 6F:
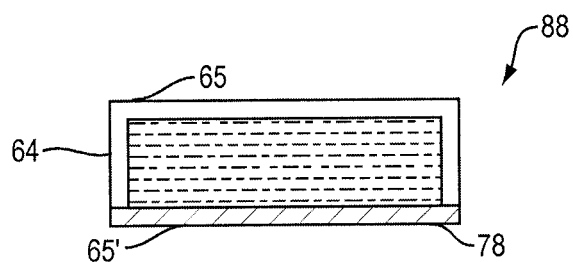
Figure 6G:
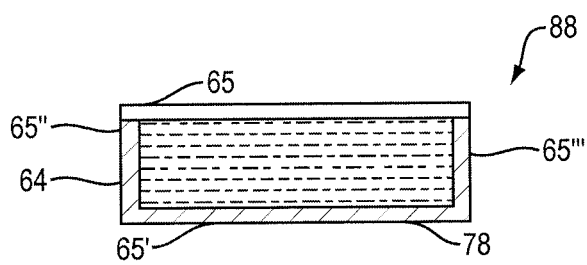

In still another embodiment, illustrated in FIG. 6D, optical reference 78 is positioned as an element separate from any wall of the reaction chamber 88 and with the long axis of the optical reference 78 parallel to at least one wall of the reaction chamber 88; illustrated in FIG. 6E, the optical reference 78 is embedded in the second wall 65' of the reaction chamber 88; illustrated in FIG. 6F, the optical reference 78 is planar and bonded to the second wall 65' of the reaction chamber 88; illustrated in FIG. 6G, the optical reference 78, forms three walls, 65', 65", 65''', with only the first wall 65 opposite to wall 65' not a portion of the optical reference 78.

Sample Preparation Cartridge

According to the embodiments of the coagulation systems 100, 100' and 100" illustrated in FIGS. 1, 2, and 3, sample preparation in this invention can be realized in various ways, from manual pipetting to an automatic fluidic control system. Non-limiting examples of microfluidic devices and methods applicable to the coagulation assay systems described above are given below. These devices and methods are not limited to assays for coagulation and can be used for a variety of wet chemical assays where metering, reagent addition, mixing, incubation and quantification of the assay reaction product is needed. Typical assays are using enzymatic reaction to measure metabolites such as lactate or creatinine or turbidimetric assays. Examples of such turbidimetric assays are agglutination assays such as latex agglutination where mono-disperse immune particles are complexing in the presence of an analyte which can be monitored by a change in turbidity.

Flow Chamber with Dry Reagent

Figure 7A:
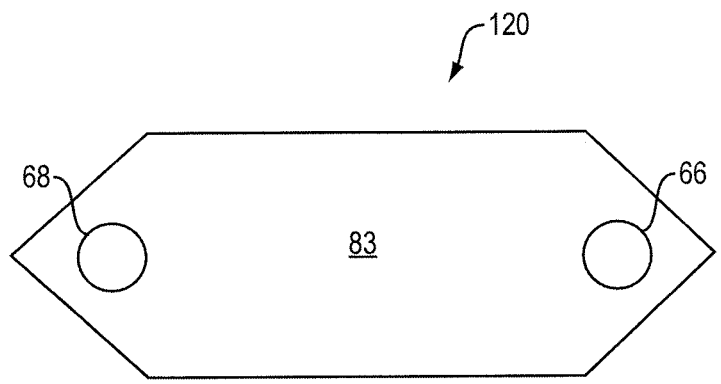
FIG. 7A is a view of the bottom of a microfluidic plate with a reaction chamber illustrating one exemplary configuration of the reaction chamber having a fluidic inlet and outlet for the sample, and dry reagent pre-stored in the chamber.
Figure 7B:
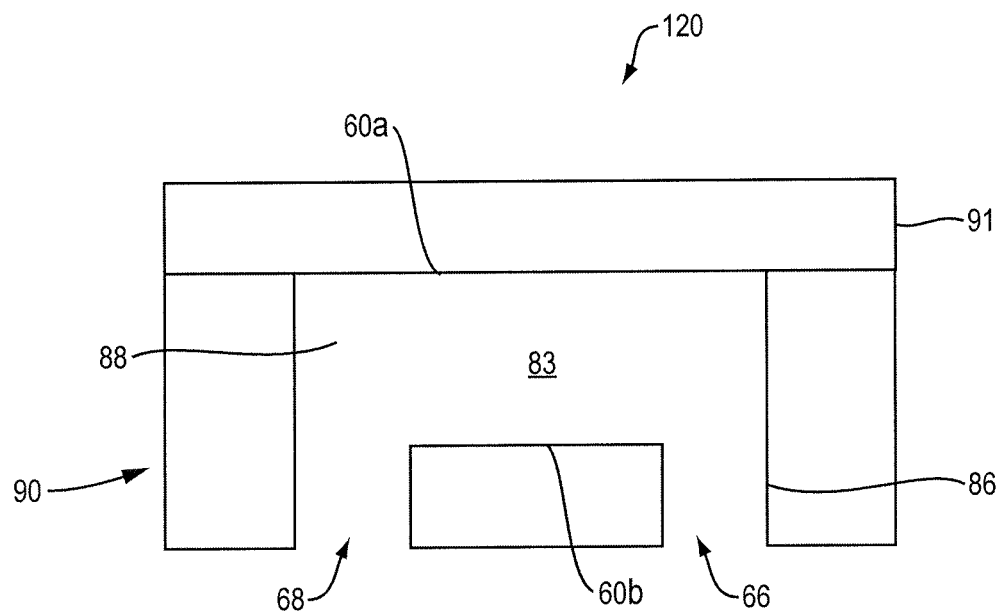
FIG. 7B illustrates a side view of FIG. 7A.

Referring now to FIGS. 7A and 7B, in one embodiment, a reaction chamber 88 of a liquid handling device 120 with a defined volume is formed by a microchannel plate 90 covered with a lid 91. The reaction chamber is used to meter the sample volume, one fluid inlet 68 is used to introduce the sample, e.g., plasma, from the bottom 60b of the reaction chamber 88, and one fluid outlet 66 at the bottom 60b of the reaction chamber 88 is used to discharge the excessive liquid from the lumen 83 of the reaction chamber 88. Dry reagent, such as lyophilized PT/APTT reagent, biotin and etc., is pre-stored in the reaction chamber 88, uniformly coated on the luminal surface of the first wall 86, for example. When the plasma fills the reaction chamber 88, the dry reagent starts to dissolve and then diffuses into the sample along the vertical direction, i.e., from the bottom 60b of the chamber 88 toward the top 60a of the chamber. The dry reagent has a relatively large contact area with the liquid sample and the diffusion distance along the vertical direction is relatively short. This configuration provides a homogeneous coagulation process across the lateral plane of the reaction chamber 88. During operation, once the chamber 88 is filled with sample, the assay process starts and the fluorescence signal acquisition begins to follow the reaction kinetics.

Flow Chamber with Liquid Reagent

FIGS. 8A-8D illustrate one embodiment of the invention illustrating a liquid handling device 120 for investigation of a sample fluid. The liquid handling device 120 comprises a reaction chamber 88, two inlet ports and channels 66 and 68 to deliver sample fluid and reagent fluid into the lumen 83 of the reaction chamber, respectively, and an outlet channel 64 for venting of the reaction chamber 88 during filling. The device 120 may contain one or more fluidic structures 68a and 64a, for example, to provide a controlled and bubble free filling of the reaction chamber lumen 83.

Figure 8B:
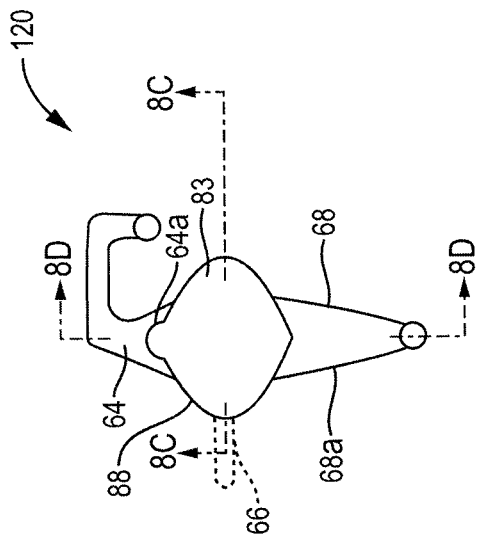
FIGS. 8A-D illustrate a liquid handling device including an exemplary configuration of the reaction chamber with two fluidic inlets; one for sample and one for reagent separately, and a fluid outlet. (A) is a perspective view of the reaction chamber; (B) is a top view of the reaction chamber; (C) is a cross-section of FIG. 8B; (D) is another cross-section of FIG. 8B.
Figure 8D:
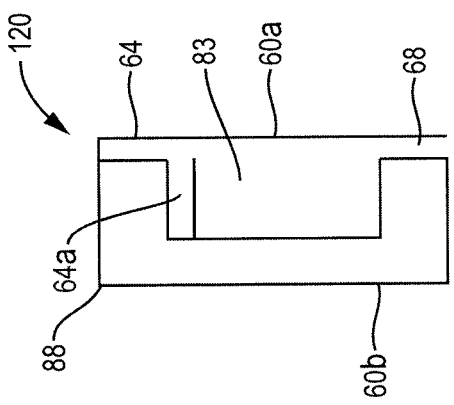
Figure 8A:
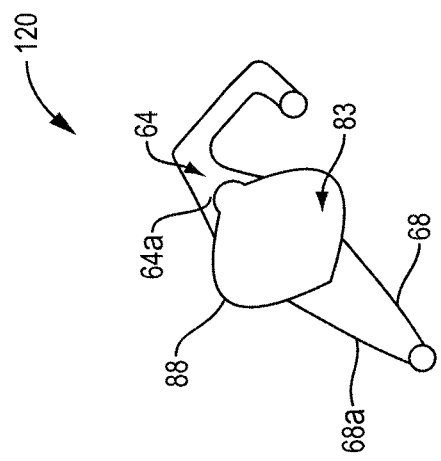
Figure 8C:
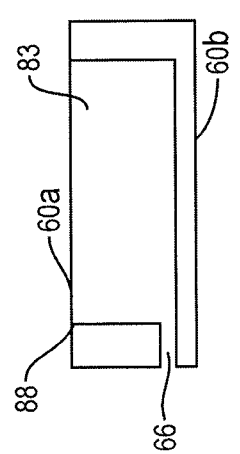
Figure 8E:
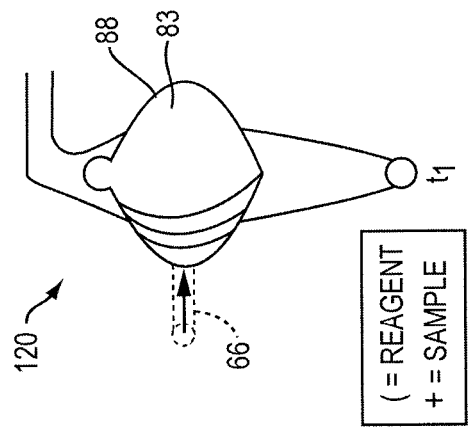
FIGS. 8E-8H illustrate sequential filling of the reaction chamber with reagent from time=0 to time=3.
Figure 8F:
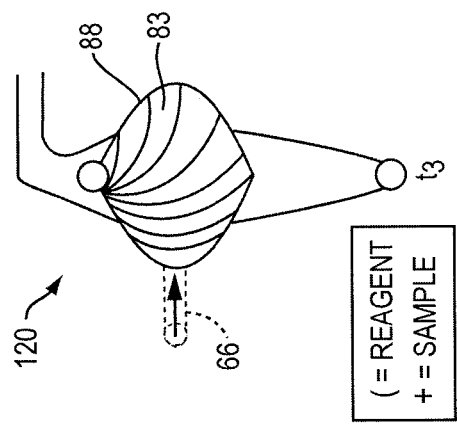
Figure 8G:
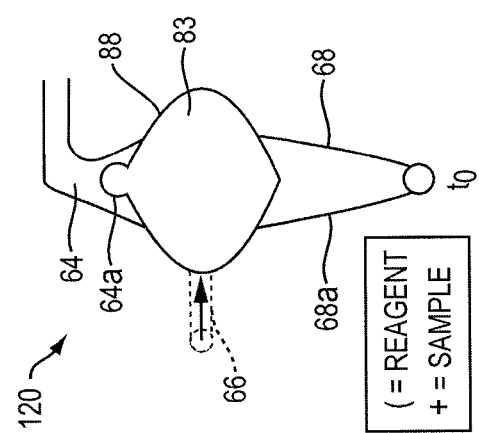
Figure 8H:
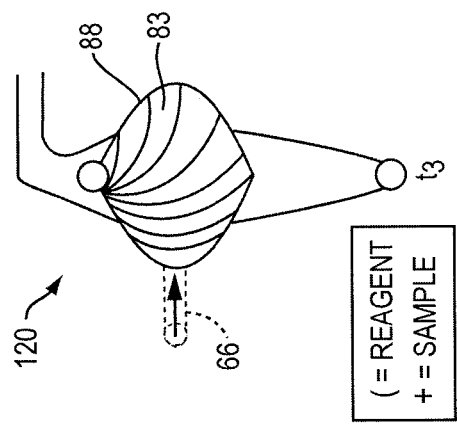
Figure 8I:
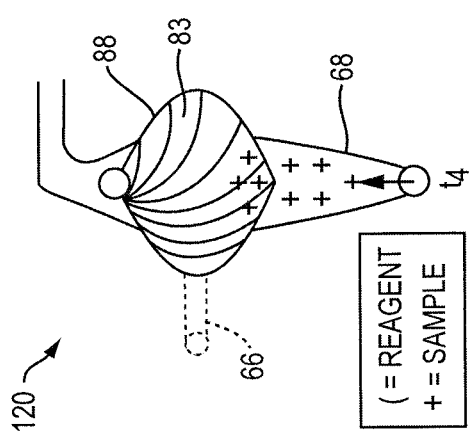
FIGS. 8I-8L illustrate the sequential filling of the reaction chamber with sample fluid from time=4 to time=7.
Figure 8J:
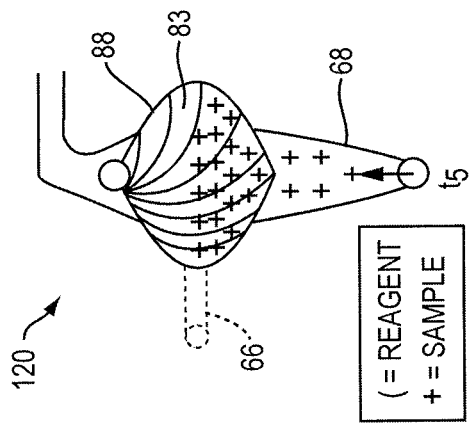
Figure 8K:
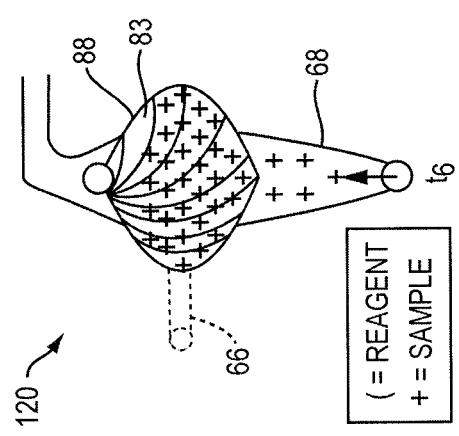
Figure 8L:
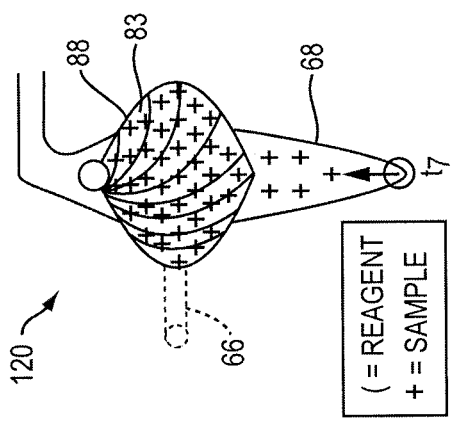

According to one embodiment of the liquid handling device 120 illustrated in FIGS. 8A-8D, the reaction chamber 88 of the device 120 is firstly filled with a metered amount of a liquid reagent via a first inlet 66. A bubble-free liquid filling can be achieved by a capillary stop feature 64a next to the outlet 64. In FIG. 8A, for example, a cylindrical groove is acting as a capillary stop 64A. A capillary stop is defined either by a sudden channel opening and by the curvature of the feature 64a or by making the outlet area 64 hydrophobic. FIGS. 8E to 8H illustrate the sequential filling of reagent into the reaction chamber 88 at different points of time from time=0, to time=3. After a metered amount of reagent has filled into the lumen 83 of the reaction chamber 88, a metered amount of sample fluid (such as plasma and whole blood) is filled into the chamber lumen 83 via the second inlet 68 as illustrated in FIGS. 8I to 8L.

Additional features of the embodiment shown on FIGS. 8A-8D follows. The liquid handling device 120 is oriented in the horizontal direction, i.e. the top view of the liquid handling device 120 is as shown on FIG. 8B. The v-Shape 68a at the inlet channel 68 has, for example, an opening angle of 30°. This v-Shape 68a could have an angle ranging from 0° to 180°, typically 15° to 120°. It is also noted that, according to this embodiment of the liquid handling device 120, the second inlet 68 and the outlet 64 is positioned on the top side 60a of the liquid handling device 120, while the first inlet 66 is positioned on the bottom side 60b of the liquid handling device 120. Other arrangements of the inlets and outlets on the top and bottom sides of the liquid handling structure are also possible and are not limited by the illustrated embodiment. The flow rate for sample and reagent may range from about 0.5 µl/s to 200 µl/s, typically 2 µl/s to 100 µl/s.

Figure 9:
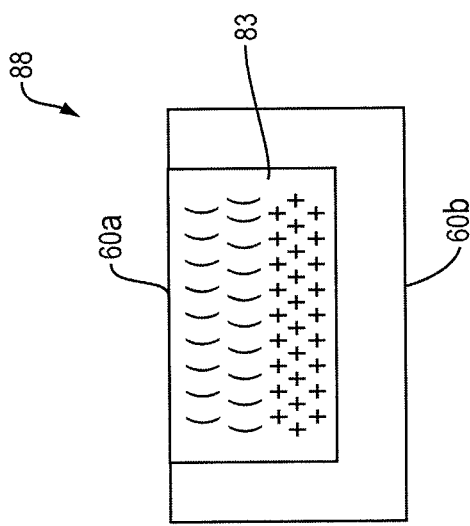
FIG. 9 illustrates a cross-section of the reaction chamber filled with reagent and sample fluid.

FIG. 9 illustratively exemplifies the reaction chamber 88 after filling of reagent and sample have been completed. Two layers are shown: a layer of reagent and a layer of sample fluid. The sample layer is spread above the reagent layer across the whole surface of the fluid in the lumen 83 of reaction chamber 88. Therefore, it generates a large contact area between the two liquids, namely reagent and sample. With this large contact area, the mixing and thereby the reaction of the reagent and sample liquids is highly efficient.

In the illustrated embodiments in FIG. 8, a v-shaped geometry of the inlet structure 68 is used to support an even distribution of the sample fluid into the reaction chamber. As illustrated in FIGS. 8c and 8d, the sample inlet 68 is connected to the top 60a of the reaction chamber 88 whereas the reagent inlet 66 is positioned in opposite to the bottom 60b of the reaction chamber 88.

Figure 10A:
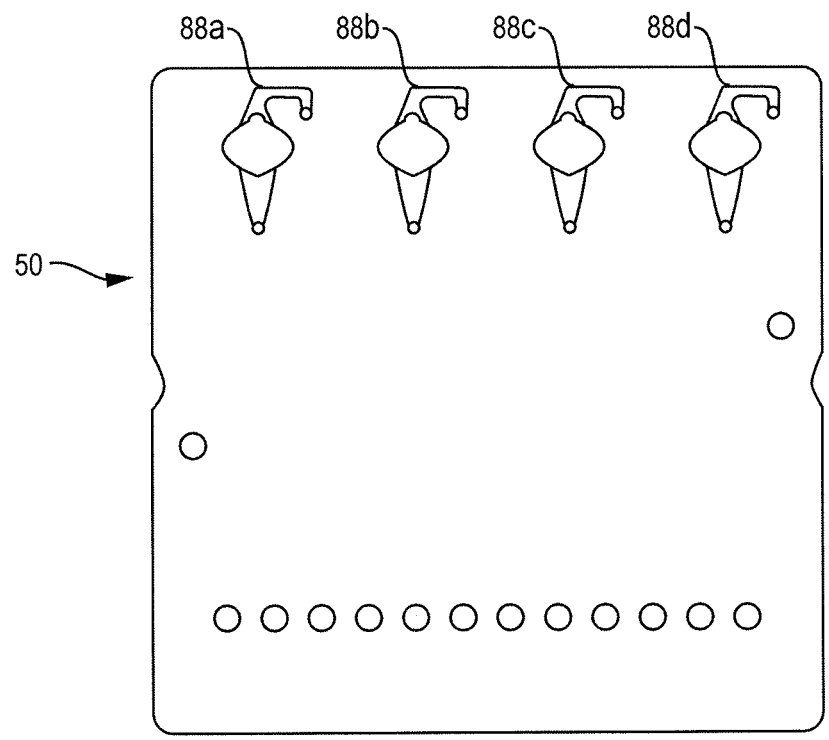
FIGS. 10A and 10B are top and bottom views, respectively, of an exemplary microfluidic device including a plurality of reaction chambers in accordance with the invention.

Referring to FIG. 10A, a top view of an embodiment of a microfluidic device 50 having four reaction chambers 88a-d is illustrated. In the illustrated embodiment, the reaction chambers 88a-d are positioned toward one side of the microfluidic device 50 but could be positioned in the microfluidic card at other positions.

Figure 10B:
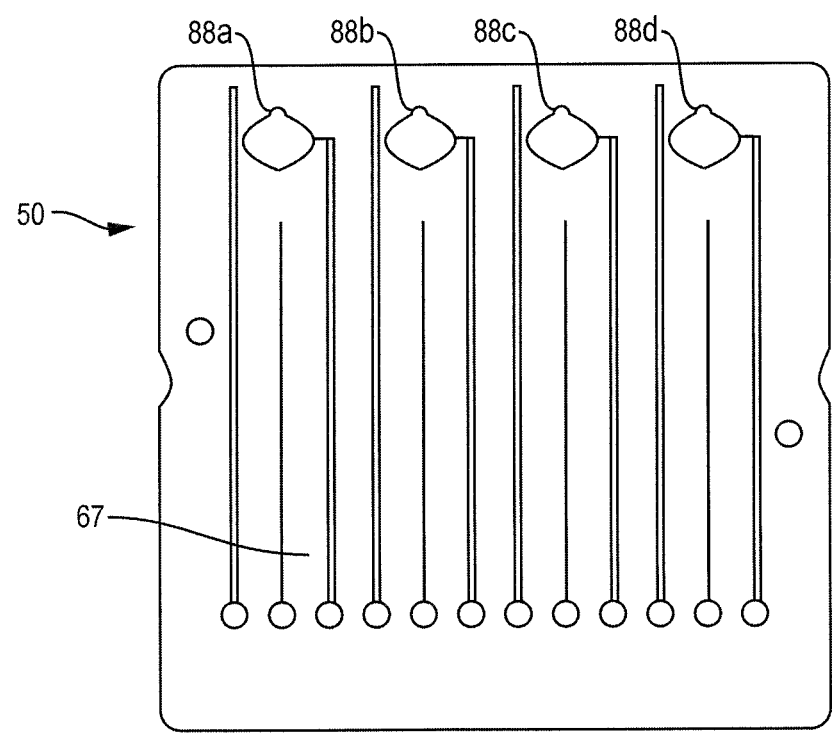

FIG. 10B illustrates a bottom view of the microfluidic card 50 including a plurality of channels 67 that are in fluid communication with the reaction chambers 88.

Exemplification/Proof of Principle

Figure 11A:
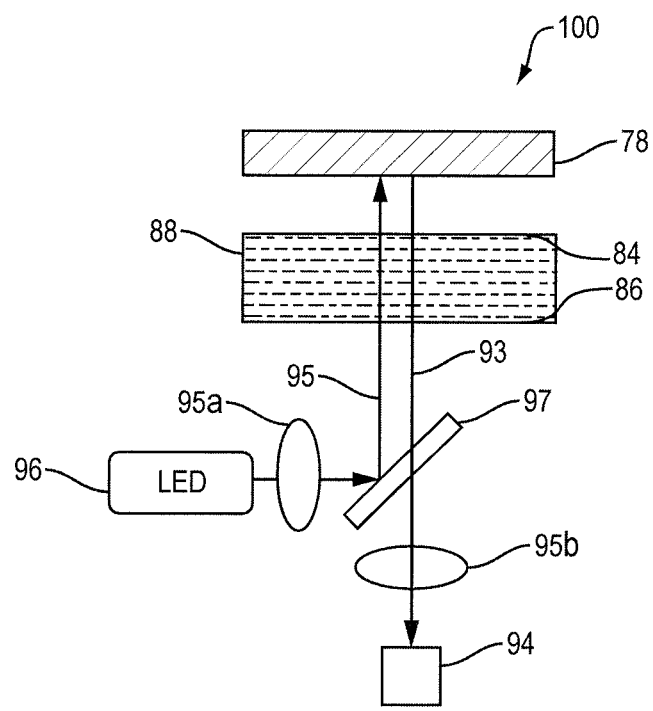
FIG. 11A shows an embodiment of the invention based on the optical configuration shown in FIG. 1, in which a LED is used as a light source, a fluorescence doped glass is used as an optical reference, and a quantitative fluorescence detector is used as an optical detection unit.

The embodiments of the coagulation systems 100, 100', 100" discussed above and their associated assay methods for detecting coagulation of a blood or plasma sample were evaluated with controlled plasma samples and reagents for PT and APTT assays. In the example of the double absorbance configuration described above with respect to FIG. 1 and illustrated in FIG. 11A, the fluorescence module applied in the method was a PMT-based Time Resolved Fluorescence (TRF) unit, fluorescence reference 78 was a Europium-doped glass, which contained precisely-controlled amount of europium and did not have photo bleach during excitation, and an LED 96 was used as a light source. A filter 95A was placed between the LED 96 and a dichroic mirror 97. A second filter 95B was placed between the detector 94 and the dichroic mirror 97. The plasma samples included normal control plasma (a) and high abnormal control plasma (b) from Instrumentation Laboratory Company (Orangeburg, N.Y.). Coagulation was initiated by introduction of a coagulation initiator.

Figure 11B:
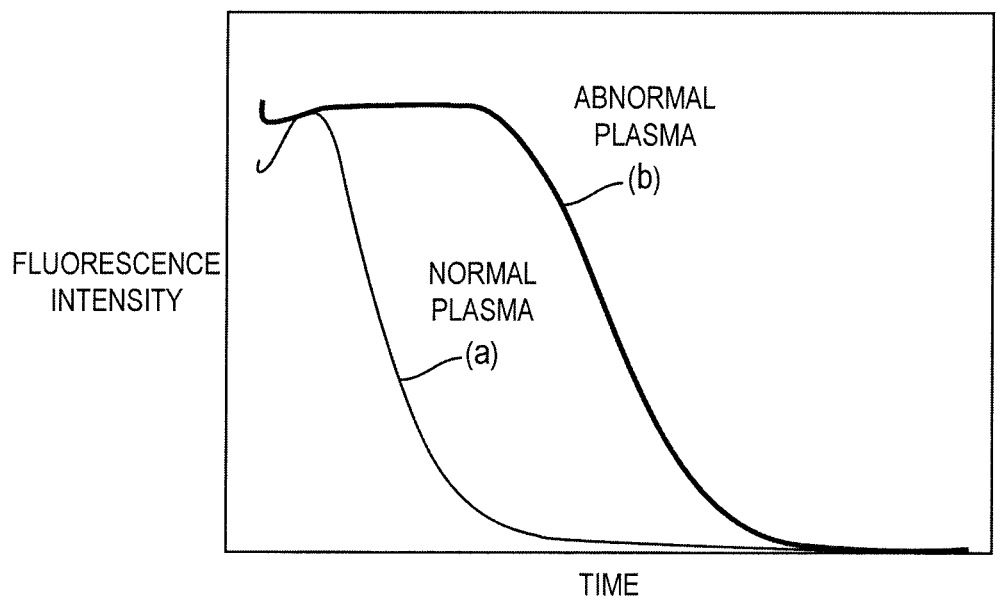
FIG. 11B illustrates a representative graph of a fluorescence signal from an assay group having abnormal plasma (b) and a control group having normal plasma (a) according to one embodiment of the double absorbance configuration of the coagulation system according to the invention shown in FIG. 11A. The abnormal assay group results show delayed signal change compared to that from the normal control assay group.

Referring to FIG. 11B, the intensity of fluorescence signal emanating from the fluorescence reference and transmitted to the fluorescence detector in the double absorbance coagulation system described above with respect to FIGS. 1 and 11A, is represented by curve (a) for normal control and a curve (b) for abnormal control plasma. In both normal and abnormal plasma samples, the fluorescence signal decreased as the coagulation initiated, propagated, and reached a stable value when coagulation was completed. The abnormal plasma takes a longer time to start and finish the coagulation process than the normal plasma.

Figure 12A:
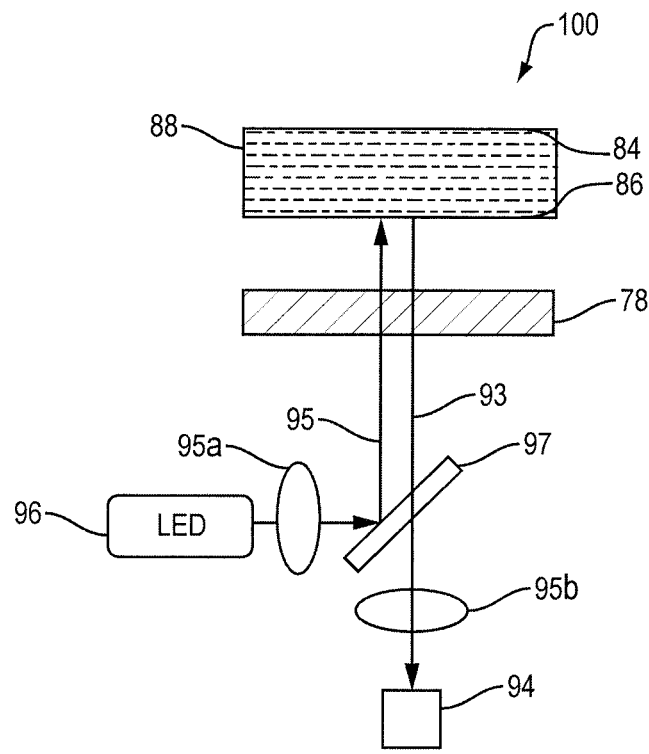
FIG. 12A shows an embodiment of the invention based on the optical configuration shown in FIG. 2 in which a LED is used as a light source, a fluorescence doped glass is used as an optical reference, and a quantitative fluorescence detector is used as an optical detection unit.
Figure 12B:
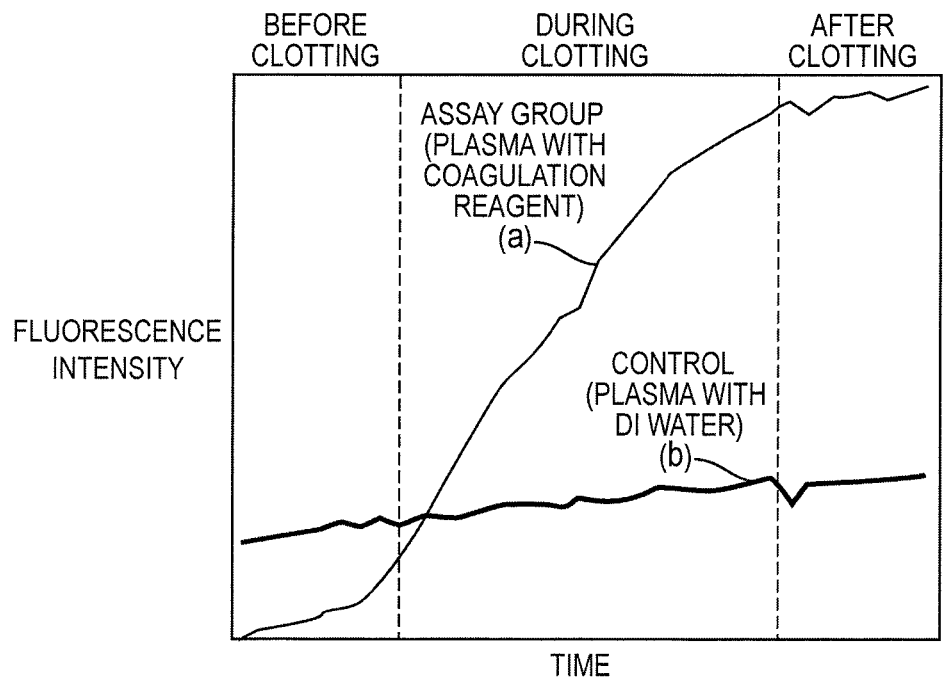
FIG. 12B illustrates a representative graph of a fluorescence signal from an assay group having coagulated plasma (a) and control group having uncoagulated plasma (b) according to one embodiment of the double absorbance configuration of the coagulation system according to the invention shown in FIG. 12A. The assay results shows enlarged signal change from the coagulated plasma (a) compared to that from plasma without coagulation (b)

Referring to FIG. 12A, an embodiment of the invention using reflection configuration described above with respect to FIG. 2 is realized. As illustrated in FIG. 12A, an LED 96 was used as the light source, a fluorescence-doped glass was used as the optical reference 78, and a quantitative fluorescence detector was used as the optical detector unit 94. A filter 95A was placed between LED 96 and a dichroic mirror 97. A second filter 95B was placed between the detector 94 and the dichroic mirror 97. The plasma samples included a normal plasma sample (a) to which a coagulation reagent was introduced and a control normal sample (b) to which water (no coagulation reagent) was introduced. The optical signal obtained from plasma with coagulation (a) and plasma without coagulation (b) is illustrated in FIG. 12B. The fluorescence signal increased on sample (a) and reached a stable value as coagulation initiated and propagated and reached a stable value when coagulation was completed. The control (b) used the same plasma sample but with the addition of deionized water no coagulation happened).

FIG. 13 shows an exemplary method to process the optical data to obtain the quantitative coagulation time. In the four steps, the original data is first normalized (FIG. 13A) and filtered (FIG. 13B) to eliminate redundant data and noise. A first order derivative (FIG. 13C) of the original data is implemented to identify the time spot when the quickest change of optical signal locates. The peak position of the first-order derivative (FIG. 13D) is used as the coagulation start time. Other methods can be used to quantitatively study the coagulation process as well.

Various modifications and other implementations of what is described and illustrated herein will occur to those of ordinary skill in the art without departing from the scope and spirit of the invention. The invention is not to be defined only by the preceding illustrative descriptions or drawings.

We claim:

1. An assay system comprising:
   a reaction chamber for holding a sample;
   an optical reference that is separate from the reaction chamber, wherein the optical reference comprises a fluorescence element, and wherein the optical reference is on a first side of the reaction chamber along an optical path;
   an excitation light source on a second side of the reaction chamber, the second side being along the optical path and being a different side than the first side, the excitation light source for directing an excitation light along the optical path through the reaction chamber to the optical reference;
   wherein the optical reference is configured to absorb at least part of the excitation light that passed through the reaction chamber and to provide an emission light responsive to absorption of the excitation light by the optical reference, the emission light being directed back through the reaction chamber towards an optical detector; and
   the optical detector that is on the second side of the reaction chamber and that is configured to detect an optical signal that is based on at least some of the emission light that passed through the reaction chamber;
   wherein a coagulation process of the sample affects transmission of light through the reaction chamber.

2. The assay system of claim 1, wherein the reaction chamber is configured to hold the sample in absence of a colorimetric reagent.

3. The assay system of claim 1, wherein the excitation light source is configured to provide a specific wavelength of the excitation light ranging from 20 nm (nanometers) to 5000 nm.

4. The assay system of claim 1, wherein the reaction chamber comprises a lumen, a planar first wall, and a planar second wall that is opposite and parallel to the planar first wall.

5. The assay system of claim 4, wherein the planar first wall and the planar second wall are each optically transparent to the excitation light in a wavelength range of about 20 nm (nanometers) to about 5000 nm.

6. The assay system of claim 5, wherein the excitation light is in a wavelength range of about 20 nm (nanometers) to about 2000 nm.

7. The assay system of claim 1, wherein the optical detector and the excitation light source are integrated.

8. The assay system of claim 4, wherein each of the first and second planar walls of the reaction chamber comprises a luminal surface, and wherein a first luminal surface associated with the first planar wall is coated with one or more reactants.

9. A method for determining coagulation time of a fluid using an optical system comprising an optical reference for providing an optical signal, the optical reference comprising a fluorescence element and the optical reference being separated by a distance from a reaction chamber holding the fluid, the method comprising:
   transmitting excitation light from an excitation light source positioned on a first side of the reaction chamber through the fluid in the reaction chamber to the optical reference, the optical reference being on a second side of the reaction chamber that is across the reaction chamber from the first side, the optical reference absorbing the excitation light transmitted through the reaction chamber;
   based on absorption of the excitation light, the optical reference transmitting emission light through the fluid in the reaction chamber to an optical detector on the first side of the reaction chamber, the optical detector detecting an optical signal based on the emission light transmitted through the fluid in the reaction chamber;
   comparing the optical signal detected by the detector to a pre-determined standard to determine the coagulation time of the fluid;
   wherein a coagulation process of the fluid affects transmission of light through the reaction chamber.

10. The assay system of claim 1, wherein the sample comprises at least one of plasma or blood.

11. The assay system of claim 1, wherein the optical reference is comprised of one or more layers of one or more optical agents, an optical agent being embedded in one or more walls of the optical reference.

12. The assay system of claim 1, wherein the optical reference is comprised of one or more layers of one or more optical agents, an optical agent being chemically or physically coated on a surface of a substrate.

13. The assay system of claim 1, wherein the optical reference comprises at least one of fluorescence doped glass, fluorescence stained glass, fluorescence dyed glass, or fluorescence materials showing a Raman effect.

14. An assay system comprising:
   a reaction chamber for holding a sample;
   an optical reference comprising a fluorescence element;
   an excitation light source for directing an excitation light through the optical reference to the reaction chamber, the optical reference being separate from the reaction chamber, and the optical reference and the reaction chamber being separated by a distance;
   the reaction chamber for providing an emission light based, at least in part, on absorption of the excitation light by the optical reference, the emission light passing through the optical reference towards an optical detector, the emission light being calibrated to a specific optical wavelength; and the optical detector that is on a same side of the optical reference as the excitation light source and that is on a different side of the optical reference than the reaction chamber, the optical detector for detecting an optical signal based on the emission light through the optical reference, the optical signal being indicative of coagulation of the sample in the reaction chamber;

wherein a coagulation process of the sample affects transmission of light through the sample and through the fluorescent element.

15. The assay system of claim 14, wherein the reaction chamber is on a first side of the optical reference and wherein the optical detector and the excitation light source are on a second side of the optical reference, the first side being opposite the second side.

16. The assay system of claim 1, wherein the fluorescence element comprises at least one of a fluorophore-doped glass, a polymer film, or a sheet containing intrinsic fluorescence.

17. The method of claim 9, wherein the fluorescence element comprises at least one of a fluorophore-doped glass, a polymer film, or a sheet containing intrinsic fluorescence.

18. The assay system of claim 14, wherein the fluorescence element comprises at least one of a fluorophore-doped glass, a polymer film, or a sheet containing intrinsic fluorescence.

19. The assay system of claim 1, wherein a distance between the optical reference and the reaction chamber is between 0 mm (millimeters) and 200 mm.

20. The method of claim 9, wherein the distance between the optical reference and the reaction chamber is between 0 mm (millimeters) and 200 mm.

21. The assay system of claim 14, wherein the distance between the optical reference and the reaction chamber is between 0 mm (millimeters) and 200 mm.

* * * * *